United States Patent
Mäkilä et al.

(10) Patent No.: US 6,898,268 B2
(45) Date of Patent: May 24, 2005

(54) IRRADIATION ADJUSTMENT IN AN X-RAY APPARATUS FOR USE IN INTRAORAL APPLICATION

(75) Inventors: Jari Mäkilä, Helsinki (FI); Reeta Ikola, Vantaa (FI); Kirsi Nykänen, Hyvinkää (FI); Tero Isoaho, Tuuaula (FI); Tapio Kotka, Maisala (FI); Vesa Varjonen, Hyvinkää (FI)

(73) Assignee: Instrumentarium Corp., Tuusula (FI)

( * ) Notice: Subject to any disclaimer, the term of this patent is extended or adjusted under 35 U.S.C. 154(b) by 0 days.

(21) Appl. No.: 10/210,857

(22) Filed: Aug. 1, 2002

(65) Prior Publication Data
US 2003/0026387 A1 Feb. 6, 2003

(30) Foreign Application Priority Data
Aug. 3, 2001 (FI) .............................................. 20011601

(51) Int. Cl.⁷ ................................................. A61B 6/14
(52) U.S. Cl. .......................................... 378/38; 378/98.7
(58) Field of Search ................................. 378/98.7, 108, 378/97, 168, 38–40, 191, 98.8

(56) References Cited

U.S. PATENT DOCUMENTS

| | | | |
|---|---|---|---|
| 3,622,785 A | 11/1971 | Irwin et al. ................... 250/77 |
| RE33,634 E | 7/1991 | Yanaki | |
| 5,331,166 A | 7/1994 | Crosetto et al. ....... 250/370.11 |
| 5,694,448 A * | 12/1997 | Morcom ..................... 378/98.8 |
| 5,784,434 A * | 7/1998 | Shieh .......................... 378/191 |
| 6,018,563 A * | 1/2000 | Arai et al. ..................... 378/39 |
| 6,038,287 A * | 3/2000 | Miles ......................... 378/117 |
| 6,042,267 A | 3/2000 | Muraki et al. .............. 378/169 |
| 6,459,765 B1 * | 10/2002 | Ganin et al. ................ 378/108 |
| 6,594,339 B1 * | 7/2003 | Alving et al. .............. 378/98.7 |

FOREIGN PATENT DOCUMENTS

| | | |
|---|---|---|
| EP | 346530 | 12/1989 |
| WO | 87/01555 | 3/1987 |

* cited by examiner

Primary Examiner—Craig E. Church
Assistant Examiner—Jurie Yun
(74) Attorney, Agent, or Firm—Andrus, Sceales, Starke & Sawall, LLP

(57) ABSTRACT

The invention relates to a method for performing X-ray imaging in intraoral application. The method comprises irradiation of an object with a substantially low amount of X-radiation, and a substantially low amount of X-radiation passed through the object is received. The method comprises compiling a sample of image data from the received, substantially low amount of X-radiation. The sample of image data information is communicated to an X-ray source (100), and according to the sample of image data information the object is irradiated with X-radiation, from which X-radiation the part that has passed through the object is received, and the received X-radiation, which is consistent with the sample of image data information, is used for compiling image information.

26 Claims, 4 Drawing Sheets

IRRADIATION ADJUSTMENT IN AN X-RAY APPARATUS FOR USE IN INTRAORAL APPLICATION

GENERAL

Figure 1:
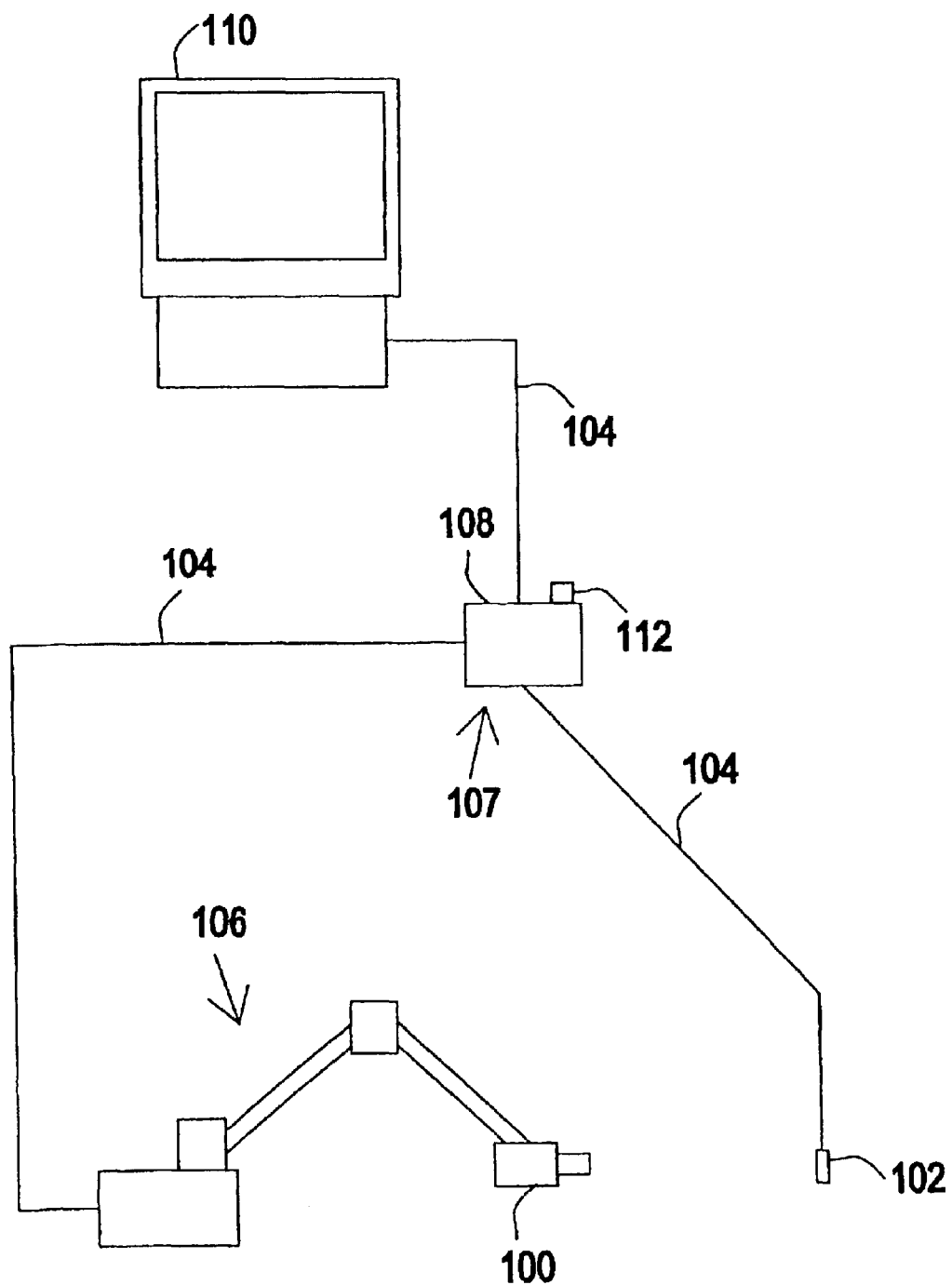

In dentistry, taking X-ray images of the teeth and jawbone structure is important for a reliable and successful examination of the teeth and jawbone structure. Intraoral applications are performed by using an intraorally placed X-ray detector for the reception of X-radiation. The X-radiation is emitted from an X-ray source outside the mouth to a point in the teeth and jaw structure to be examined.

PRIOR ART

The X-ray detector is placed in the mouth typically by using special retainers. The object to be imageized is irradiated with X-radiation, which is produced by an extraoral X-ray source. The X-radiation that has passed through the object is received by an X-ray detector. Positioning of the X-ray detector in the mouth and alignment of X-radiation can be varied for imaging various parts of the teeth and jaw structure (maxilla and mandible).

The prior art includes an intraoral solution, wherein a person who operates X-ray imaging selects irradiation values on the basis of his or her experience and the manufacturer's instructions. Such irradiation values include exposure time, electrical anode current, and electrical anode voltage. Electrical anode current has an impact on radiation intensity and, together with exposure time, on radiation dosage. Electrical anode voltage has an impact on the spectrum of X-radiation. Enhancement of electrical anode voltage increases the transmission capacity of X-radiation.

A drawback in the prior art technology is inaccurate X-ray imaging, which results in a poor quality of image and/or a patient receiving an excessive amount of X-radiation. One reason for a patient to receive an excessive amount of X-radiation is for example that the X-ray image is a failure and the X-ray imaging procedure has to be repeated. Another alternative for excessive X-irradiation is that the X-ray image is indeed successful, yet has been produced with an unnecessarily high quantity of X-radiation.

Poor image quality is extremely unfortunate in X-ray imaging processes as it undermines possibilities of providing a reliable diagnosis. In the worst scenario, there may even be a human life at stake in a failed diagnosis. Poor picture quality and a patient's overexposure are both results of the fact that the selection of irradiation or exposure values is inaccurate in the prior art solution.

BRIEF DESCRIPTION OF THE INVENTION

The inventive solution provides an improved X-ray imaging solution for intraoral applications, wherein the X-ray imaging is performed in an automated fashion with an optimal quantity of X-radiation. This is achieved by a method for performing X-ray imaging in an intraoral application, in which method X-radiation is generated for irradiating an object and X-radiation passed through the object is received for compiling image information, and data is transmitted between the generation and reception of X-radiation for performing X-ray imaging.

The invention relates also to an X-ray arrangement for use in intraoral application for performing X-ray imaging on an object, said X-ray arrangement comprising an X-ray source for generating X-radiation for an object, and an X-ray detector for receiving X-radiation passed through the object for compiling image information. The X-ray arrangement comprises a data transfer link between an X-ray source and an X-ray detector for transmission of data between the X-ray source and the X-ray detector for performing X-ray imaging.

The invention relates further to a method for performing X-ray imaging in intraoral application. The method comprises irradiating an object with a substantially low amount of X-radiation, receiving a substantially low amount of X-radiation passed through the object, compiling a sample of image data from the received, substantially low amount of X-radiation, transmitting the sample of image data information to an X-ray source, exposing the object to X-radiation in accordance with the sample of image data information, the X-irradiation passed through the object being received from said X-radiation, and the received X-radiation consistent with the sample of image data information being used for compiling the image information.

The invention results as well to an X-ray arrangement for performing X-ray imaging on an object, said X-ray arrangement comprising an X-ray source for exposing an object to X-radiation, and an X-ray detector for receiving X-radiation passed through the object for compiling image information. The X-ray apparatus comprises a data transfer link between the X-ray source and the X-ray detector, and processing instruments for controlling the X-ray source to irradiate an object with a substantially low amount of X-radiation, the X-ray detector receiving the X-radiation passed through the object from said X-radiation for compiling a sample of image data and said processing instruments and data transfer link being used for supplying the X-ray source with a sample of image data information, according to which the object is irradiated by the X-ray source.

The invention is based on establishing a data transfer link between an X-ray source and an X-ray detector, whereby information is transmitted between the generation and reception of X-radiation. The information being transmitted can be exploited for optimal X-ray imaging.

The invention is also based on using a sample of image data, compiled with a substantially low amount of X-radiation, as a basis for performing optimal X-irradiation on an object for producing an X-ray image.

In the inventive solution, X-ray imaging is performed in an automated manner with an optimal amount of X-radiation. Hence, the overexposure of an object or patient to X-radiation will be avoided. Another benefit achieved is that high quality X-ray images are obtained for diagnoses, which may be of crucial importance in terms of making correct diagnoses.

LIST OF FIGURES

Figure 2:
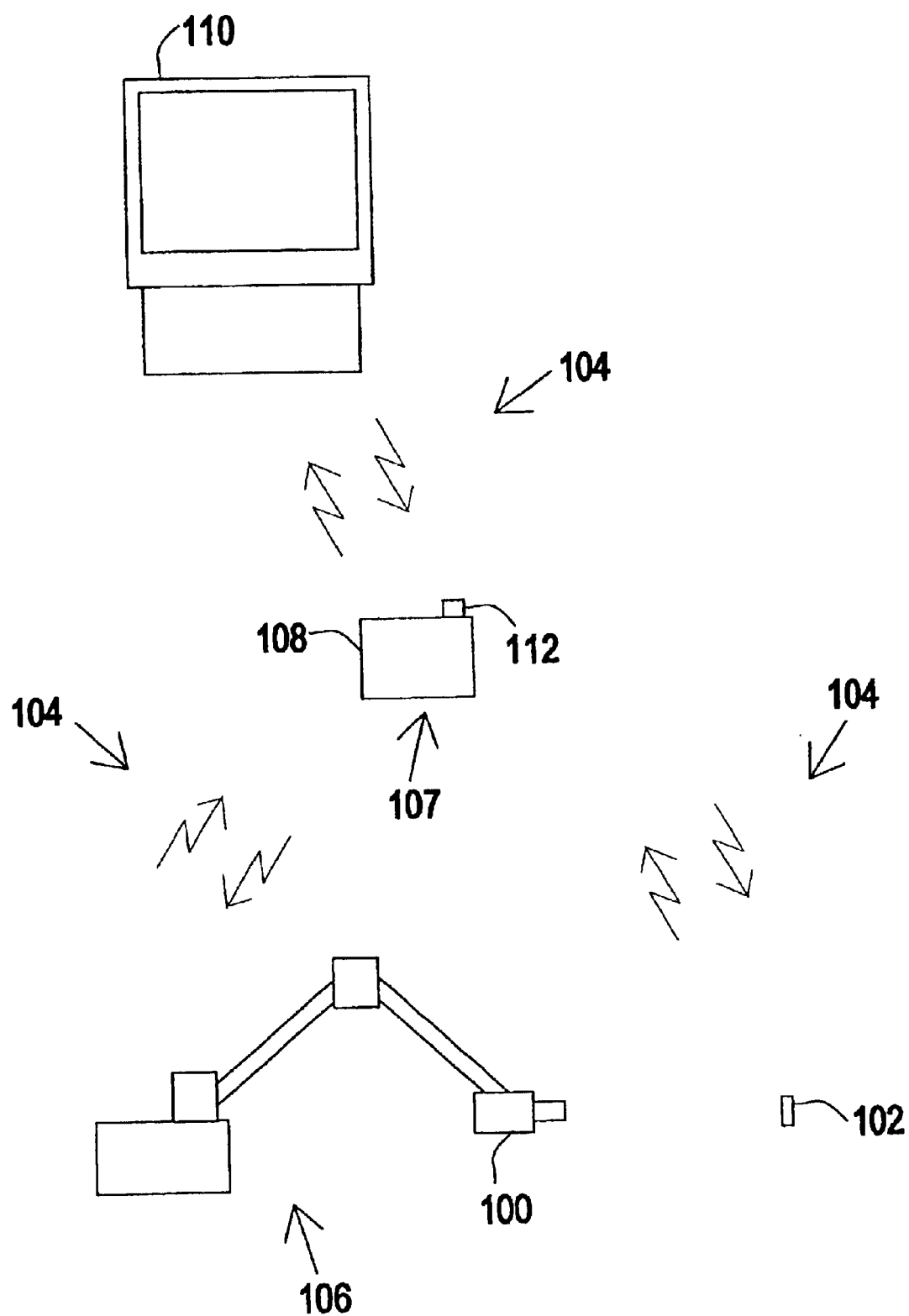
Figure 3:
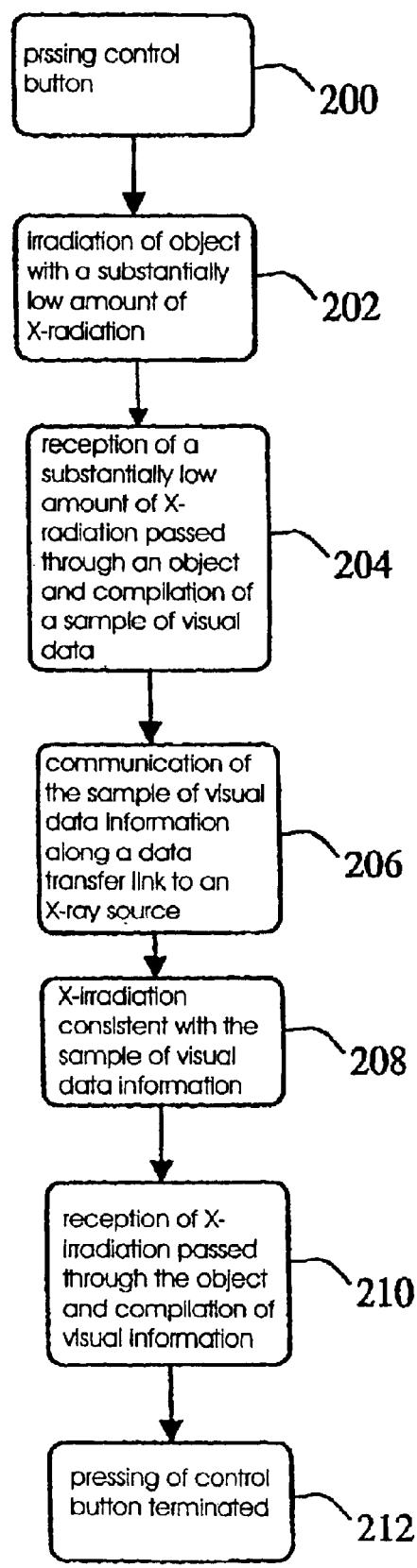
Figure 4:
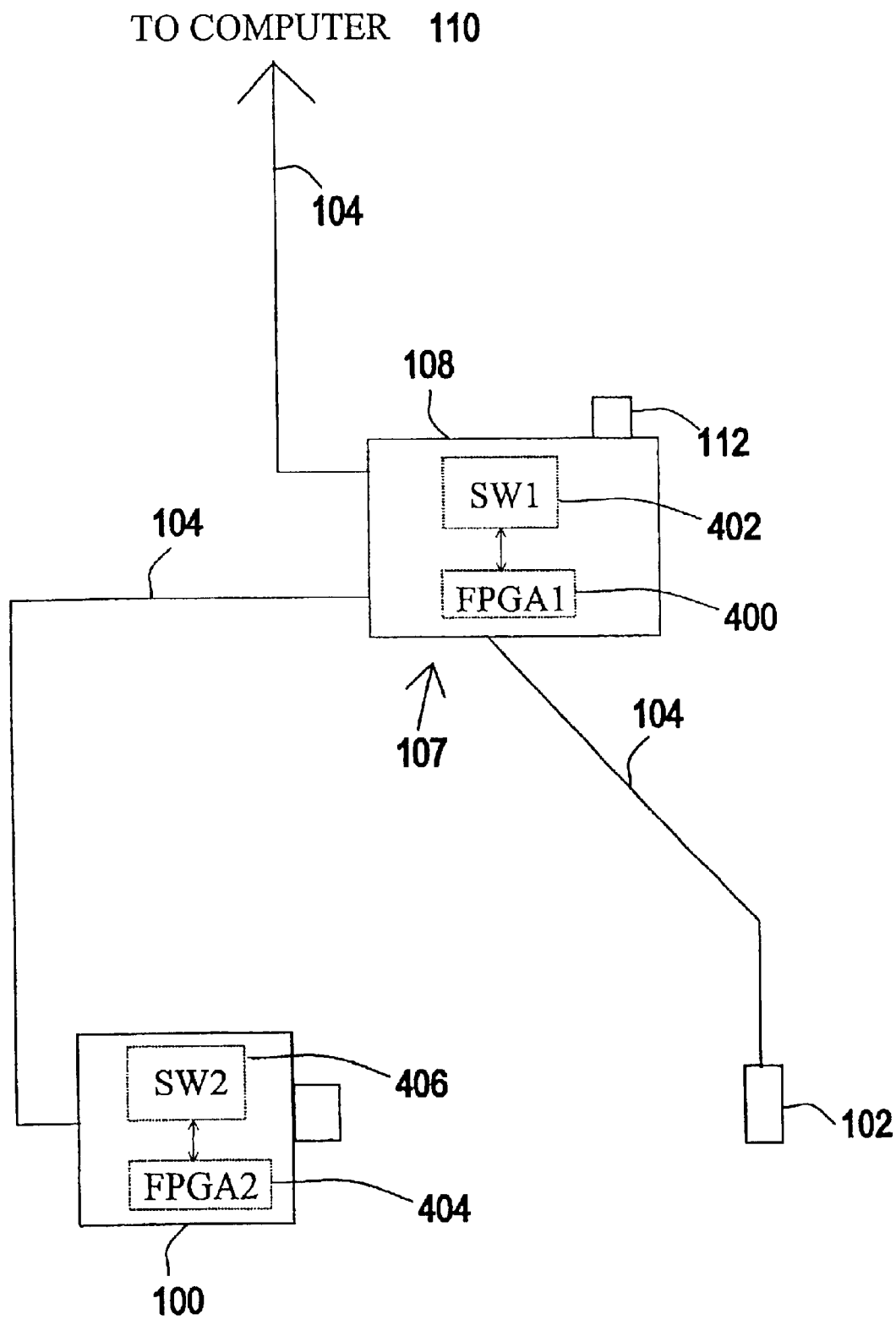

FIG. 1 shows an X-ray arrangement of the invention, which employs wired data transfer communications and which is used for intraoral application, FIG. 2 shows an X-ray arrangement of the invention, which employs wireless data transfer communications and which is used for intraoral application, FIG. 3 shows a method according to another preferred embodiment of the invention in a block diagram, and FIG. 4 shows an exemplary implementation for processing instruments.

The inventive X-ray arrangement for use in intraoral application, which is depicted in FIG. 1, comprises an X-ray source 100 for producing X-radiation, an X-ray detector 102 for receiving X-radiation passed through an object, and a data transfer link or communication 104 between the X-ray source and the X-ray detector. The X-ray source comprises an X-ray tube and typically also a collimator. The X-ray source is preferably carried by a linkage 106, whereby the X-ray source can be set in various radiating positions. The X-ray detector comprises preferably a digital image sensor, which is divided in a multitude of imaging zones or pixels.

The X-radiation passed through an object and received by the X-ray detector is used for compiling image information. The X-ray arrangement comprises processing instruments 108 for processing the image information. The processing instruments are implemented by means of processor electronics or some other prior art electronics. The processor instruments 108 are housed in their container 107 along the data transfer link 104 between the X-ray detector 102 and the X-ray source 100. It is also conceivable to place the processing instruments in the X-ray detector or the X-ray source. The inventive X-ray arrangement may have connected thereto a computer unit 110 by way of the data transfer link 104. It is possible to establish a data communication from the computer unit to the processing instruments 108, the X-ray detector 102, and/or to the X-ray source 100. The processing instruments can also be housed in the computer unit. The data transfer links 104 are wired or wireless. FIG. 1 illustrates an X-ray arrangement of the invention making use of wired data transfer links 104, and FIG. 2 shows an X-ray arrangement of the invention making use of wireless data transfer links 104. A wired data transfer link or communication is set up by means of prior known cable solutions. A wireless data transfer link is implemented by means of prior known transceiver solutions. In preferred embodiments of the invention, the X-ray arrangement and the data transfer link are established by means of digital technology.

The inventive X-ray arrangement can also be implemented in such a way that some of the data transfer links are wireless and others are wired. For example, the data transfer link to the computer unit 110 can be wireless, while the data transfer link between the X-ray detector 102, the processing instruments 108, and the X-ray source 100 is wired. The computer unit may be located at a substantial distance from the X-ray source, X-ray detector and processing instruments. It should also be appreciated that the inventive X-ray arrangement does not necessarily have a computer unit 110 connected thereto by way of a data transfer link.

The X-ray arrangement comprises a control button 112 for initiating an X-ray imaging process. The control button is in engagement for example with the processing instruments. Under current (year 2001) official regulations, the control button comprises a so-called "dead man's switch", wherein an X-ray imaging process is initiated and sustained with the control button pressed all the way down. And, as the time of keeping the control button all the way down exceeds the duration of an X-ray imaging process (e.g. 100 milliseconds), the pressing time exceeding the duration of the X-ray imaging process has of course no consequence regarding the duration of the X-ray imaging process. The control button can also be located for example in engagement with the linkage 106.

In a first preferred embodiment of the invention, the X-ray apparatus for use in intraoral application comprises an X-ray detector 102, which is positioned in the mouth by means of separate retainers on a part or spot of the teeth and jaw structure desired to be imaged by X-ray imaging. The X-ray apparatus comprises an X-ray source 100, used for developing X-radiation for a spot to be imaged. From the X-radiation emitted by the X-ray source, the X-ray detector receives the X-radiation passed through the object for compiling image information. In the first preferred embodiment of the invention, the X-ray apparatus comprises a data transfer link 104 established between an X-ray source and an X-ray detector, along which is transmitted data between the X-ray detector and the X-ray source having a functional effect on both.

In further reference to the first preferred embodiment of the invention, the image information can be worked with processing instruments 108, for example in such a way that the image information is used to provide at least one irradiation or exposure parameter with an impact on a function of the X-ray source, such as for example on exposure time, radiation dosage, radiation intensity, radiation spectrum, and radiation transmittance. Electrical anode current has an impact on radiation intensity and, together with exposure time, on radiation dosage. Electrical anode voltage has an impact on the spectrum of X-radiation. Enhancement of electrical anode voltage increases the transmittance of X-radiation.

A second preferred embodiment of the invention is also associated with FIGS. 1 and 2. In addition, FIG. 3 depicts the second preferred embodiment of the invention in a process block diagram. Thus, the sequences or method steps described hereinbelow are in reference to those shown in FIG. 3.

In a first method step or sequence 200 of the second preferred embodiment of the invention, the control button is pressed for initiating an imaging process. In a second method step 202, the X-ray source 100 irradiates an object with a substantially low amount of X-radiation. A substantially low amount of X-radiation implicates that an object is irradiated with an amount of X-radiation which is 0.1%–50% of the amount of radiation contained in actual X-irradiation. A substantially low amount of X-radiation comprises preferably 1%–10% of the amount of radiation contained in actual X-irradiation.

In a third method step 204, the X-ray detector 202 receives a substantially low amount of X-radiation passed through an object. The received, substantially low amount of X-radiation is used to compile a sample of image data. In a fourth method step 206, the sample of image data information is conveyed to an X-ray source. The sample of image data information may refer to a complete image data sample. In this case, the processing instruments 108, used for necessary processing of the image data sample, are located in connection with an X-ray source. In cases other than the above, the sample of image data information refers to a sample of image data processed by means of the processing instruments 108, in which processing the sample of image data is worked to provide at least one irradiation parameter. The irradiation parameter is consistent with what has been described above in reference to the first preferred embodiment of the invention. Hence, the sample of image data information comprises for example a complete sample of image data or at least one irradiation or exposure parameter.

In a fifth method step 208, the actual X-irradiation is performed, wherein an object is irradiated by the X-ray source 100 according to a sample of image data information. In a sixth method step 210, the X-ray detector 102 receives the X-radiation irradiated according to the sample of image data information and passed through the object for compiling image information. In various steps of the second preferred embodiment of the invention, the control button 112, the processing instruments 108, and data transfer links 104 are utilized as necessary. Under current (year 2001)

official regulations, a final method step 212 of the second preferred embodiment of the invention comprises terminating the pressing of the control button.

In embodiments of the invention, communicating information along the data transfer link 104 occurs in a one-way or a two-way mode. The following examples may also be relevant. Information is transmitted by an X-ray source along a data transfer link to an X-ray detector. The X-ray detector receives said information and adapts its function on the basis of the received information. Such functional adaptation implicates, for example, that the X-ray detector adopts a standby condition for the reception of X-radiation. The X-ray detector transmits the information along a data transfer link to the X-ray source. The X-ray source receives the information and adapts its function on the basis of the received information. Such functional adaptation implicates, for example, that the X-ray source initiates irradiation of an object immediately or after a certain delay time.

FIG. 4 depicts an exemplary implementation for the processing instruments 108. What is shown in FIG. 4 and described hereinbelow in reference thereto is related by way of example both to the first and to the second preferred embodiment of the invention. Some of the processing instruments are housed in their container 107 along the data transfer link 104. The container 107 houses electronics 400, implemented by an FPGA (Field Programmable Gate Array) logic circuit, and a microprocessor 402 comprising a software application. The electronics 400 is used to perform functions relating to the upkeep of the data transfer link 104, and/or data processing, which may comprise, for example, processing in relation to the compilation of an irradiation or exposure parameter. Instead of an FPGA logic circuit, the electronics 400 can be implemented by some other means, such as for example by asic-electronics or discrete components. The electronics 400 comprises preferably a programmable logic circuit, such as for example said FPGA logic circuit. The microprocessor 402 and its associated software application are used to perform data processing, such as for example the compilation of an irradiation or exposure parameter or some of the processing relating to the compilation of an irradiation parameter.

The X-ray source 100 is respectively provided with electronics 404, implemented by an FPGA logic circuit, and a microprocessor 406 comprising a software application. The electronics 404 is used to perform functions relating to the upkeep of the data transfer link 104, and/or data processing, which may comprise, for example, processing in relation to the compilation of an irradiation or exposure parameter. Instead of an FPGA logic circuit, the electronics 404 can be implemented by some other means, such as for example by asic-electronics or discrete components. The electronics 400 comprises preferably a programmable logic circuit, such as for example said FPGA logic circuit. The microprocessor 406 and its associated software application are used to perform data processing, such as, for example, processing in relation to the compilation of irradiation values. Data processing in the microprocessor 406 may also relate to the compilation of an irradiation or exposure parameter or some of the processing relating to the compilation of an irradiation parameter.

In further reference to FIG. 4 and to the inventive solutions, the arrangement of a microprocessor and electronics, such as for example an FPGA logic, can be different from what is shown in FIG. 4. They can also be arranged in such a manner, for example, that the container 107 houses some FPGA logic and the X-ray source 100 is provided with a microprocessor setup, comprising a software application. It is also conceivable that the positions of a microprocessor and electronics be arranged in such a way that the container 107 does not necessarily exist but, instead, a microprocessor and electronics are mounted in connection with the X-ray source 100 and the X-ray detector 102 or, for example, in connection of just the X-ray source 100.

Technical implementations more detailed than those disclosed above have not been described in the present context, because such implementations are feasible in terms of hardware, electronics, and software by using prior known solutions. The data to be communicated over data transfer links comprises data in a prior known mode. Since the inventive X-ray apparatus is preferably implemented with digital technology, the data is preferably in a bit mode.

Although the invention has been described above with reference to the accompanying figures and specification, the invention is by no means limited to those, but the invention can be diversified within the scope defined by the claims.

What is claimed is:

1. A method for performing intraoral X-ray imaging that shortens read out time between a test X-ray exposure and a full X-ray exposure, the method comprising the steps of:
   irradiating an object with a test exposure comprising a dose of a substantially low amount of X-radiation;
   providing a digital image sensor that receives the dose of substantially low amount of X-radiation after the dose is passed through the object;
   compiling a sample of image data information from the received dose of substantially low amount of X-radiation;
   conveying the sample of image data information to an X-ray source;
   irradiating the object according to the sample of image data information with a full X-ray exposure comprising a larger dose of X-radiation, the larger dose of X-radiation being received by the digital image sensor after it passes through the object; and
   compiling image information from the received large dose of X radiation, the image information being consistent with the sample of image data information.

2. A method as set forth in claim 1, characterized in that X-ray imaging is performed in a digitalized manner.

3. A method as set forth in claim 1, characterized in that the sample of image data information is communicated between the initial reception and later generation of X-radiation, which has an impact on the later generation of X-radiation.

4. A method as set forth in claim 1, wherein the digital image sensor is divided into a plurality of imaging zones or pixels.

5. A method as set forth in claim 1, characterized in that at least one irradiation parameter is calculated from the sample of image data.

6. A method as set forth in claim 5, characterized in that the irradiation parameter comprises a setting for exposure time.

7. A method as set forth in claim 5, characterized in that the irradiation parameter comprises a setting for anode current, which has an impact on radiation intensity.

8. A method as set forth in claim 5, characterized in that the irradiation parameter comprises a setting for anode voltage, which has an impact on the transmittance of X-radiation.

9. A method as set forth in claim 1, characterized in that the sample of image data information comprises at least one irradiation parameter.

10. A method as set forth in claim 1, characterized in that data is communicated along a wired data transfer link.

11. A method as set forth in claim 1, characterized in that data is communicated along a wireless data transfer link.

12. A method as set forth in claim 1, characterized in that data is communicated in a digitalized manner along a data transfer link.

13. An X-ray arrangement for use in intraoral application for performing X-ray imaging of an object, said X-ray arrangement comprising an X-ray source for irradiating an object with X-radiation and an X-ray detector comprising a digital image sensor for receiving X-radiation passed through the object for compiling image information, characterized in that the X-ray arrangement comprises:

a data transfer link between the X-ray source and the X-ray detector, and processing instruments whereby the X-ray source is controlled to irradiate an object with a test exposure comprising a substantially low amount of X-radiation, from which low amount of X-radiation the X-ray detector receives the X-radiation passed through the object for compiling a sample of image data, and said processing instruments and data transfer link being used for supplying the X-ray source with a sample of image data information, according to which the X-ray source irradiates the object.

14. An X-ray arrangement as set forth in claim 13, wherein the X-ray detector comprises a digital image sensor that is divided into a plurality of imaging zones or pixels.

15. An X-ray arrangement as set forth in claim 13, characterized in that the X-ray arrangement comprises processing instruments for calculating at least one irradiation parameter from a sample of image data.

16. An X-ray arrangement as set forth in claim 15, characterized in that the sample of image data information comprises at least one irradiation parameter.

17. An X-ray arrangement as set forth in claim 15, characterized in that the irradiation parameter comprises a setting for exposure time.

18. An X-ray arrangement as set forth in claim 15, characterized in that the irradiation parameter comprises a setting for anode voltage, which has an impact on radiation intensity.

19. An X-ray arrangement as set forth in claim 15, characterized in that the irradiation parameter comprises a setting for anode voltage, which has an impact on the transmittance of X-radiation.

20. An X-ray arrangement as set forth in claim 13, characterized in that the X-ray arrangement is implemented with digital technology.

21. An X-ray arrangement as set forth in claim 13, characterized in that the X-ray arrangement comprises a computer unit for processing image information.

22. An X-ray arrangment as set forth in claim 21, characterized in that between the X-ray source and the computer unit is established a data transfer link.

23. An X-ray arrangement as set forth in claim 21, characterized in that between the X-ray detector and the computer unit is established a data transfer link.

24. An X-ray arrangement as set forth in claim 13, characterized in that the data transfer link is wired.

25. An X-ray arrangement as set forth in claim 13, characterized in that the data transfer link is wireless.

26. An X-ray arrangement as set forth in claim 13, characterized in that the X-ray arrangment comprises a data transfer link implemented with digital technology.

* * * * *